US008679552B2

(12) United States Patent
Guthery

(10) Patent No.: US 8,679,552 B2
(45) Date of Patent: *Mar. 25, 2014

(54) ACNE VULGARIS TREATMENT REGIMEN

(71) Applicant: B. Eugene Guthery, Texarkana, TX (US)

(72) Inventor: B. Eugene Guthery, Texarkana, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/658,674

(22) Filed: Oct. 23, 2012

(65) Prior Publication Data

US 2013/0289005 A1 Oct. 31, 2013

Related U.S. Application Data

(63) Continuation of application No. 13/140,559, filed as application No. PCT/US2009/068587 on Dec. 17, 2009, now Pat. No. 8,313,782.

(60) Provisional application No. 61/138,579, filed on Dec. 18, 2008.

(51) Int. Cl.
*A01N 65/00* (2009.01)

(52) U.S. Cl.
USPC ........................................... 424/725

(58) Field of Classification Search
None
See application file for complete search history.

(56) References Cited

U.S. PATENT DOCUMENTS

| | | | |
|---|---|---|---|
| 4,299,826 A | 11/1981 | Luedders | |
| 5,443,844 A | 8/1995 | McDaniel | |
| 5,445,823 A | 8/1995 | Hall et al. | |
| 5,482,710 A | 1/1996 | Slavtcheff et al. | |
| 5,612,324 A | 3/1997 | Guang Lin et al. | |
| 5,696,169 A | 12/1997 | Otsu et al. | |
| 5,962,517 A | 10/1999 | Murad | |
| 6,039,950 A | 3/2000 | Khwaja et al. | |
| 6,110,908 A | 8/2000 | Guthery | |
| 6,174,892 B1 | 1/2001 | Gormley et al. | |
| 6,262,117 B1 | 7/2001 | Sefton | |
| 6,482,839 B1 | 11/2002 | Thornfeldt | |
| 6,492,326 B1 | 12/2002 | Robinson et al. | |
| 6,558,656 B2 | 5/2003 | Mann | |
| 6,576,660 B1 | 6/2003 | Liao et al. | |
| 6,673,374 B2 | 1/2004 | Murad | |
| 6,696,484 B2 | 2/2004 | Liao et al. | |
| 6,943,197 B2 | 9/2005 | Maibach et al. | |
| 7,198,807 B2 | 4/2007 | Anderson et al. | |
| 7,238,377 B2 | 7/2007 | Piccirilli et al. | |
| 7,314,634 B2 | 1/2008 | Hernandez et al. | |
| 8,003,690 B2 | 8/2011 | Vernault et al. | |
| 2003/0175234 A1 | 9/2003 | Hernandez et al. | |
| 2004/0234632 A1 | 11/2004 | Piccirilli et al. | |
| 2006/0067892 A1 | 3/2006 | Vergnault et al. | |
| 2006/0110481 A1 | 5/2006 | Majeed et al. | |
| 2006/0159714 A1 | 7/2006 | Thorel | |

OTHER PUBLICATIONS

Liang, T., et al. "Inhibition of Steroid 5a-Reductase by Specific Aliphatic Unsaturated Fatty Acids." Biochem J. Jul. 1992, vol. 285 (pt 2), pp. 557-562: table 1; abstract; p. 557, col. 1, para 1.

*Primary Examiner* — Michael Meller
(74) *Attorney, Agent, or Firm* — D. Scott Hemingway; Hemingway & Hansen, LLP

(57) ABSTRACT

A kit for treatment of acne vulgaris, said formulation of the kit effectively inhibiting or killing *Proprionibacterium* without antibiotics. A preferred formulation alleviates the four pathogenic factors of acne.

In a preferred method using the kit, a first skin-wash formulation comprising a higher zinc pyrithione concentration than the second leave-on formulation is applied to the affected area and subsequently washed off the skin with water. Then, a second leave-on formulation, preferably comprising a minimum of 0.25% zinc pyrithione with additional ingredients for eliminating or reducing other pathogenic factors of acne vulgaris, is applied to the skin.

The kit includes a skin-wash component and a leave-on component comprising the acne treatment of the invention. Formulations are preferably applied as creams, lotions or emulsions.

21 Claims, No Drawings

ACNE VULGARIS TREATMENT REGIMEN

CROSS REFERENCE TO RELATED APPLICATIONS

This application is a continuation of U.S. application Ser. No. 13/140,559, filed on 17 Jun. 2011, which is a National Stage of International Application Number PCT/US09/68587, filed on 17 Dec. 2009, which claims the benefit of U.S. Provisional Application No. 61/138,579 filed on 18 Dec. 2008.

STATEMENT REGARDING FEDERALLY SPONSORED RESEARCH OR DEVELOPMENT

Not applicable.

TECHNICAL FIELD OF INVENTION

The present invention relates to regimens, including formulations and methods for the treatment of acne vulgaris.

BACKGROUND OF THE INVENTION

Acne vulgaris is a chronic inflammatory disease of the skin which can cause an undesirable appearance on the face, back and other areas of the body. The skin comprises sebaceous glands which secrete sebum, an oily substance which is a mixture of fat and the debris of dead fat-producing cells. These cells are constantly replaced by new growth at the base of the sebaceous glands. In humans, sebaceous glands are primarily found in association with hair follicles but also occur in hairless areas of the skin, except for the palms of the hand and soles of the feet. A pilosebaceous unit consists of a sebaceous gland, a hair shaft, a hair follicle, and an erector pili muscle which causes the hair to stand up when it contracts. The follicle comprises cells which are involved in hair production and corneocytes of the epidermal layer of the skin lining the follicles. Generally the sebum is deposited on the hairs inside the follicles and is brought up to the surface of the skin along the hair shaft. In hairless areas, the sebum surfaces through ducts.

While sebum serves the purpose of lubricating and protecting the hair and skin and preventing drying and irritation of membranes, it may also be detrimental if it is blocked from exiting the follicle or duct. In acne vulgaris, desquamated (shed) follicular cells and sebum may form a plug which blocks the excretion of sebum from the follicle. This manifests as a "whitehead" also called a closed comedone. Though different theories have been proposed for the dark color of another type of skin blemish commonly known as a "blackhead," it has been reported that oxidized sebum oil (perhaps mixed with other substances such as melanin) may be responsible. This oxidized oil may harden in the follicle, contributing to the plugging of the normal sebum drainage of the follicle.

*Propionibacterium acnes*, is an anaerobic bacterium and has been reported to be the primary pathogenic agent involved with the development of inflammatory acne and comedogenesis. The plugged follicle provides a favorable anaerobic environment complete with a nourishment source (sebum) for the organism. Overgrowth of *Propionibacterium acnes* has been reported to cause destruction of the lining of the follicle, which allows follicular material to enter the dermis

*Propionibacterium acnes* hydrolyzes the oil in the sebum, thereby causing the release of free fatty acids. This release of free fatty acids into the surrounding tissue due to rupture of the sebaceous gland causes inflammation. Certain terminology has been generally ascribed to skin blemishes resulting from inflammation, while recognizing that categorization may be subjective to a certain extent. A "pustule" is terminology ascribed to a skin blemish resulting from inflammation very near the surface of the skin. A "pimple" is terminology ascribed to a skin blemish resulting from deeper inflammation. A "cyst" is terminology ascribed to a skin blemish resulting from still deeper inflammation.

While many approaches to acne treatment have been reported, some have advocated use of a systemic or topical agent to address the overgrowth of *Propionibacterium acnes*.

Systemic therapy requires prescription antibiotics, such as erythromycin, tetracyclines, and clindamycin, however in recent times physicians have become reluctant to over-prescribe antibiotics because resistance may be developed by not only acne-causing bacteria but other bacteria which are the causative agents of other more serious diseases. Furthermore, systemic administration may cause systemic side effects, as relatively high levels of the drug must circulate throughout the entire body.

Topical antibiotics which have been utilized to attempt to inhibit the overgrowth of *Propionibacterium acnes* are clindamycin, erythromycin, tetracycline, and metronidazole. Each of these topical antibiotics reportedly cause side effects and widespread use also contributes to the risk of bacterial resistance.

DETAILED DESCRIPTION

It has now been found that acne vulgaris may be effectively treated by applying one or more antibiotic-free topical compositions to the affected area. Disclosed herein is a regimen and formulations which in a preferred embodiment addresses one or more, and preferably all, of the pathogenic factors in acne: a) the putative pathogen of acne, *Propionibacterium acnes*; b) abnormal desquamation of sebaceous-follicle epithelium (comedogenesis); c) the androgen-induced excessive sebum production; and d) the follicular reactivity (inflammation).

In a preferred treatment regimen, two distinct formulations are sequentially applied to the affected area as disclosed herein: a first skin wash formulation and a second leave-on formulation, each of which comprise zinc pyrithione (IUPAC name bis(2-pyridylthio)zinc 1,1'-dioxide), but in different concentrations.

Zinc pyrithione is also known as zinc omadine, ZnP or pyrithione zinc. Its molecular formula is $C_{10}H_8N_2O_2S_2Zn$. Hereinafter, zinc pyrithione will be referred to as ZPT.

A first skin wash composition comprises a higher concentration of ZPT than the leave on composition. The ZPT concentration in the skin wash is from about 1.0% up to about 2.5% ZPT. Most preferably, about 2.0% ZPT is utilized, which is approximately 20,000 ppm.

ZPT has low solubility in water (8 ppm or 0.00080 ppm at neutral pH), nor is it very soluble in any organic solvent. In order to prepare any composition with ZPT it is necessary to suspend the ZPT in an emulsion.

A surfactant is utilized in making the formulation comprising ZPT. A preferred surfactant is a non-ionic, non-toxic surfactant which is suitable for application to human skin, such as a difunctional block copolymer surfactant. Most preferred is the difunctional block copolymer surfactant which terminates in primary hydroxyl groups and is commercially available under the trade name Pluronic F68 (BASF Corporation, Mount Olive N.J.).

Another method of suspending the ZPT is to utilize a combination of a hydroxycellulose thickener with sodium polynapthalene polysulfonate.

The 2.0% ZPT formulation also preferably comprises a pharmaceutical excipient which forms an emulsion comprising all ingredients. A non-ionic hydroxypropyl cellulose thickener, stable at acid pH in the presence of an emulsifier (glycerol monostearate, glycerol monolaurate, Polawax) makes it possible to suspend the insoluble ZPT. A preferred thickener is sold under the brand Klucel. A combination of Klucel and an excipient is used to create an emulsion with a viscosity greater than 1,000 centipoises (the viscosity of the 48% zinc Omadine (ZPT) sold by Arch Biocides). In this fashion, the insoluble zinc Omadine does not precipitate to the bottom but is held in the emulsion.

Initially, the water or alcohol is stirred rapidly while the Klucel is poured in a very fine stream. If any small clumps of Klucel are added to the water or alcohol solution, dissolution will not likely occur. Complete hydration of the Klucel will take from one to ten hours. Once the Klucel is completely hydrated the mixture has a much greater viscosity. In a preferred formulation, the sodium laureth sulfate or equivalent (serving as a surfactant) will be added next, followed by cetylpyridinium chloride. Cetylpyridinium chloride (CPC) is a cationic quaternary ammonium compound that is accepted in the art for use in personal care products and to which antiseptic activity is attributed. Salicylic acid is added to the mixture and mixed well.

Under high shear, zinc pyridinethione is added. In a commercial format of a 48% suspension, about 4.17 cc per total of 100 cc is used. Any fragrance components desired, such as Fresh Scent, are then added to the formulation, followed by q. s. to 100 cc with deionized water. The combination of Klucel and Polawax is capable of suspending the insoluble ZPT in an emulsion. Other ingredients with similar properties may be used to suspend the ZPT in an emulsion.

Salicylic acid and resorcinol, known active ingredients for the treatment of acne, may be improved by formulating an emulsion of ZPT with the addition of salicylic acid and/or resorcinol. An example is provided in the table below. Note that the table below and others throughout the specification provide examples for a 100 cc volume. To make a larger volume, the amounts should be scaled up proportionally.

| Ingredient | Amount |
| --- | --- |
| Salicylic Acid | 0.50 grams |
| Zinc pyrithione | 2.00 percent by weight |
| | 4.17 cc of the 48% microfine suspension |
| Pluronic F 68 | 10 cc |
| Klucel HFNF | 0.50 grams |
| Cetylpyridinium chloride | 0.10 grams |
| Sodium laureth sulfate | 2.00 grams |
| Fragrance | Q.S. |
| Deionized water | Q.S. to 100 cc |

In the preferred method of the invention, the first skin wash formulation is applied to the affected area and washed off after about 1 minute to about 30 minutes. Most preferably, the first skin wash formulation is washed off after between about 1 minute and 20 minutes. Preferably, the first skin wash formulation is left on for about 10 minutes. While not being bound to any particular mechanism of action, it is believed that ZPT in the first skin wash formulation will solubilize in sebum and localize in the hair follicles, where it will kill bacteria harbored there that contribute to acne vulgaris. In addition, after about three to five minutes contact with human skin and hair the ZPT binds irreversibly to the human skin and into the sebaceous glands. Even after the skin is rinsed there remains a large reservoir of ZPT bound to the skin. Repeated use can result in a desired accumulation.

In a subsequent step of the preferred method, a second formulation comprising ZPT in an amount of 0.25% ZPT (2500 ppm) or less is applied to the skin and left on indefinitely. For example, as part of a bedtime routine of face care, a user will first apply the first skin wash formulation, rinse it off with water, and then pat the skin dry with a towel. Subsequently, the user will apply the second formulation and leave it on the affected area of the skin while retiring for the night in order to enhance the formulation's activity against the putative causes of acne.

The two step process and accompanying formulations described herein provides the user with a regimen that effectively inhibits or eradicates *Propionibacterium* species. *Propionibacterium acnes* (*P. acnes*), *Propionibacterium avidum* and *Propionibacterium granulosum* are strains of anaerobic bacteria which may play a role in acne vulgaris. Representatives of all three species of diphtheroids can be found on the skin surfaces of normal individuals, as well as acne patients, in different proportions related to the sampled skin region, patient's age, and to the presence of acne lesions.

In a preferred leave-on composition, other effective anti-acne ingredients are employed along with said ZPT. One or more fatty acids or fatty acid esters selected from the following unsaturated fatty acids, in decreasing preference, may be employed: gamma-linolenic acid>cis 4,7,10,13,16,19-docosahexaenoic acid=cis-6,9,12,15-octatetraenoic acid=arachidonic acid (5,8,11,14 eicosatetraenoic acid)=alpha-linolenic acid>linoleic acid>palmitoleic acid>oleic acid>myristoleic acid.

Pure linoleic acid (octadeca-9,12 dienoic acid) has been reported in the art to exhibit antimicrobial effects against *Propionibacterium* strains, and pure linoleic acid may be utilized in the formulation of the invention to provide increased beneficial antibacterial properties.

It has now been found that hydrolysates of linoleic acid may be employed in an acne treatment methodology. These hydrolysates provide a cost benefit in the manufacturing of the formulations as compared with pure linoleic acid, but surprisingly are as effective as the pure fatty acid.

In a preferred embodiment, a formulation for treating and preventing acne comprises hydrolysates of unsaturated fatty acids which are from about 56% to 70% linoleic acid. Several appropriate linoleic acid hydrolysates are manufactured by Cognis Oleochemicals, (Cognis USA, Cincinatti, Ohio). For example, Edenor SB 05 (CAS 67701-06-8) may be used as a linoleic acid hydrolysate. It contains between 56% and 70% linoleic acid and may be employed in the formulation in a concentration of 0.1% to 25%. Preferably, between about 0.1% and 10% and most preferably between 2% and 5% by volume will be used. The most preferred concentration is 2.5% by volume.

Another suitable source for linoleic acid is the product Emersol 315 (CAS 60-33-3) which contains 60% alpha linoleic acid and is manufactured by Cognis Oleochemicals.

It is necessary in the preparation of a stable acne treatment product containing an unsaturated fatty acid that an antioxidant be added to prevent oxidation of the fatty acid upon exposure to air. In order to enhance the functionality of a product, an antioxidant may be employed which itself has a beneficial effect on the acne treatment process, such as gallic acid esters, especially propyl gallate, Vitamin E (alpha tocopherol), butylated hydroxytoluene (BHT) and nordihydroguaiaretic acid (NDGA). Alternatively, single use vials or containers can be employed with the formulation bottled or packaged under inert gas, such as nitrogen gas, in order to avoid oxidation.

Another non-antibiotic approach to inhibit or kill the *Proprionibacterium* species is employment in a formulation for the treatment thereof of the fatty acid ester glycerol monolaurate. The preferred concentration of glycerol monolaurate is 2 grams per liter, but it may be employed in the range of from 0.5 to about 5 grams per liter.

Most preferably, the formulation further comprises a suitable pharmaceutically acceptable carrier, preferably a cream, lotion or an emulsion in which ZPT is suspended.

Specific pharmacological carriers, formulation types, treatment regimens may vary. By "pharmaceutically acceptable," such as in the recitation of a "pharmaceutically acceptable carrier," or a "pharmaceutically acceptable derivative," is meant a compound that is not biologically or otherwise undesirable, i.e., the compound may be incorporated into a topical formulation of the invention and administered to a patient without causing any undesirable biological effects or interacting in a deleterious manner with any of the other components of the formulation in which it is contained. A "pharmacologically active" compound refers to an active agent as defined above, or to an analog or derivative thereof having the same type of pharmacological activity as the parent compound.

Excipients can be added to the formulation to improve the composition's appeal, such as fragrance, silicone, and humectants, such as glycerin or sorbitol. Excipients may also include those ingredients known in the art to aid in solubilizing, suspending, emulsifying or otherwise stabilizing the active ingredients of the formulation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method and formulations of "treating" a patient, as the term is used herein, thus encompasses both prevention of the acne in a predisposed individual and treatment of acne in a clinically symptomatic individual.

By an "effective" amount or a "therapeutically effective amount" of a pharmacologically active agent is meant a nontoxic but sufficient amount of the drug or agent to provide the desired effect, i.e., prevention or treatment of acne. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term "topical administration" is used in its conventional sense to mean delivery of a topical drug or pharmacologically active agent to the skin, as in, for example, the treatment of an inflammatory dermatosis such as acne vulgaris.

"Carriers" or "vehicles" as used herein refer to pharmaceutically acceptable carrier materials suitable for topical drug administration. Carriers and vehicles useful herein include any such materials known in the art which are nontoxic and do not interact with other components of the composition in a deleterious manner.

Another aspect of acne vulgaris which is addressed by the preferred formulation of the invention is the earliest morphological change in a sebaceous follicle associated with acne vulgaris, namely abnormal follicular epithelial differentiation. In this abnormal differentiation, cornified cells in the upper section of the follicular canal become abnormally adherent. Instead of undergoing the normal process of shedding and discharge through the follicular orifice, these cells form a compact hyperkeratotic plug (comedo) in the follicular canal.

It is preferred that one or more components be included in a formulation which will prevent the comedo from forming or will cause it to be released. The agents which may be added to address this objective are linoleic acid, salicylic acid, resorcinol, Vitamin A and/or Vitamin A analogs, and retinaldehyde.

Linoleic acid has already been discussed in the context of antibacterial properties. If not employed in the formulation for its antibacterial properties, it may be employed as an anticomedogenic agent.

Another preferred component of the formulation is salicylic acid. Salicylic acid is an approved over-the-counter drug for the topical treatment of acne in concentrations of 0.5% to 2.0%. In these concentrations salicylic acid is moderately comedolytic.

Another preferred component of the topical formulation is Vitamin A and/or a Vitamin A analog. Most preferably, retinaldehyde, which is a natural precursor of retinoic acid, is employed in the formulation. Retinaldehyde in a concentration of 0.1% is as effective at preventing comedones as other topical vitamin A products, but without the toxicity or irritation associated with those products. In addition, retinaldehyde, as opposed to other topical vitamin A analogs, has a significant in vitro antibacterial activity against gram-positive bacteria likely due to the isoprenoic lateral chain. The preferred concentration of retinaldehyde is in a range from 0.01% to 1.0% with the most preferred being 0.1%.

Anti-androgens are compounds which prevent androgens from expressing their activity at target sites, and are differentiated from compounds which have central hypothalamic action or act directly on the gonads to inhibit androgen secretion. Sebaceous glands and hair follicles are androgen-sensitive tissues. The activity of testosterone in stimulating sebum production by sebaceous glands has been inhibited in a preferred embodiment of the present invention by employment of an inhibitor of the enzyme 5 alpha-reductase ("5AR") which prevents conversion of testosterone to dihydrotestosterone (DHT).

There are two reported types of 5 alpha-reductase, type 1 and type 2. Activity of the type 1 isoenzyme predominates in sebaceous glands, where it may be involved in regulation of sebum production. Inhibition of the type 2 enzyme is associated with erectile dysfunction (ED), ejaculatory dysfunction (EjD) and decreased libido.

In the preferred formulation of the invention, a 5AR inhibitor that is selective for type 1 inhibition is utilized. Specific unsaturated aliphatic fatty acids may be employed as 5AR inhibitors. The relative inhibitory potencies of unsaturated fatty acids are, in decreasing order: gamma-linolenic acid>cis 4,7,10,13,16,19-docosahexaenoic acid=cis-6,9,12,15-octatetraenoic acid=arachidonic acid=alpha-linolenic acid>linoleic acid>palmitoleic acid>oleic acid>myristoleic acid. These compounds are effective at concentration ranges of 0.10 to 0.20 milliMolar. The methyl esters and alcohol analogues of these compounds, glycerols, phospholipids, saturated fatty acids, retinoids and carotenes are all inactive.

Purified unsaturated aliphatic fatty acids may be expensive, and it has been found that fractionated products that contain effective levels of the specific aliphatic fatty acids may be employed as 5AR inhibitors. Gamma-linolenic acid is found in Borage Oil and Evening Primrose Oil in concentrations of nearly twenty-five percent, and these oils may be fractionated to obtain gamma-linolenic acid. An alternate source for alpha-linoleic acid and linoleic acid are hydrolysates, examples of which are Emersol 305 and 315 manufactured by Cognis, Inc. in Cincinnati, Ohio.

It is preferred that concentrations of 0.01% to 10% of the aliphatic unsaturated fatty acids containing gamma-linolenic acid, alpha-linolenic acid and linoleic acid, singly or in combination obtained from hydrolysates of oils, be used. The most preferred concentrations are from 0.1% to 2.5% by volume.

Other possible androgen receptor blockers (ARB) are lauric acid ethyl ester, linoleic acid ethyl ester and/or beta-sitosterol. The following concentrations will work to provide the ARB function: ethyl laurate—130 nanoMolar, ethyl linoleic acid—6 microMolar, and beta-sitosterol—about 10 microMolar. The saw palmetto berry is disclosed in U.S. Pat. No. 6,039,950 to block the androgen receptor, but it may contain variable amounts of the lipids noted above and provide inconsistent results. It has been found that ethyl laurate alone or in combination with beta-sitosterol, both of which are readily commercially available, are effective even without the other components of saw palmetto berries.

In an alternative embodiment, the formulation further comprises zinc cation and/or azelaic acid.

Zinc cation, such as is available from zinc sulfate, is a potent inhibitor of 5 alpha-reductase activity at concentrations of 3 to 9 milliMolar. At high concentrations, zinc is capable of completely inhibiting the enzyme activity. In addition, a zinc salt such as zinc sulfate prevents discoloration of the formulation making the final product a more aesthetically pleasing white color. Pyridoxine hydrochloride (Vitamin B6) potentiates the inhibitory effects of zinc salts. Zinc sulfate and pyridoxine hydrochloride (Vitamin B6) are both water soluble and easy to formulate into topical products to produce reduction in 5 alpha-reductase activity. Zinc sulfate should be used in concentrations of at least 1.5 milliMolar plus concentrations of pyridoxine hydrochloride of at least 0.02 percent. The addition of Vitamin B6 (0.025%) to zinc sulfate (1.5 to 3 milliMolar/liter) results in a two fold increase in the inhibition of 5 alpha-reductase.

Azelaic acid, a nine carbon dicarboxylic acid, at concentrations as low as 0.2 milliMolar, is also a potent 5AR inhibitor. Concentrations of azelaic acid at 3 milliMolar are completely inhibitory. Azelaic acid is very difficult to formulate into topical products due to solubility problems.

Most preferably, a zinc salt, pyridoxine hydrochloride and azelaic acid are all utilized in the formulation. If all three are used together at very low concentrations, which concentrations are ineffective alone, 90% inhibition of 5 alpha-reductase activity may be achieved.

In another embodiment, the 5AR inhibitor of the formulation of the invention comprises (–)catechin-3-gallate, (–)epicatechin-3-gallate and epigallocatechin 3-gallate (EGCG). EGCG shows potent inhibition in cell-free but not in whole-cell assay systems. Replacement of the gallate ester in EGCG with long-chain fatty acids produces potent 5 alpha-reductase inhibitors that are active in both cell-free and whole-cell assay systems. Concentrations required are greater than 50 microMolar per liter. These compounds, used singly or in combination, may be used to achieve blockade of 5 alpha-reductase.

Other flavonoids that are potent inhibitors of the type-1 5 alpha-reductase include myricetin, quercitin, baicalein, fisetin, alizarin, anthrarobin, gossypol, nordihydroguaiaretic acid, caffeic acid phenethyl ester, and octyl, lauryl, and dodecyl gallates. Additionally, octyl, lauryl, and dodecyl gallates are lipid soluble which allows them to penetrate the cell membrane of the sebocyte to inhibit the intracellular 5 alpha red uctase.

The primary antioxidative ingredient in green tea (*Camellia sinensis*) extract is green tea catechins (GTC), comprised of four major epicatechin derivatives; epicatechin epigallocatechin, epicatechin gallate, and epigallocatechin gallate (EGCG). Green tea is also known to contain flavonoids such as quercetin and myricetin. Green tea extract may be used as a source of these catechins and flavonoids.

Isoflavonoids and dietary lignans may be used as 5AR inhibitors. Genistein, biochanin A and equol are the most potent inhibitors of 5 alpha-reductase activity by isoflavonoids, each resulting in greater than 80% inhibition at a concentration of 100 microMolar.

Of the lignans, enterolactone is the most potent inhibitor of 5 alpha-reductase.

A natural oil from the gourd family as disclosed by Piccirilli, et al. in U.S. Pat. No. 7,238,377, which is herein incorporated by reference, has been reported to be an inhibitor of 5 alpha-reductase activity. Concentrations required are greater than 50 microMolar per liter.

As an alternative to the 5AR inhibitor, an inhibitor of androgen metabolism may be employed in the formulation. One such inhibitor is glycyrrhetinic acid in concentrations equal to or greater than 4 microMolar which suppresses 17-beta-hydroxysteroid dehydrogenase activity. This enzyme normally acts to converts A-dione (which has been converted from dehydroepiandrosterone to A-dione in the sebaceous glands) to testosterone. By suppressing this activity with glycyrrhetinic acid, testosterone formation is inhibited in the area of the sebaceous glands and therefore this minimizes the formation of DHT.

Lignans and isoflavonoids also inhibit 17-beta-hydroxysteroid dehydrogenase activity and may be employed in the formulation.

The androgen receptor can also be blocked by combinations of oral progesterone and spironolactone. These ingredients are pharmaceuticals available by prescription only. It may be undesirable to employ such pharmaceuticals if contraindicated by the patient's gender or physical condition.

It is also preferred to include an ingredient in the formulation which reduces inflammation which may be a part of the manifestation of acne vulgaris. It has been found that reducing the amount of eicosanoids formed by the lipoxygenase pathway will reduce the inflammation in the skin of patients with acne. The lipoxygenase pathway can be inhibited by certain antioxidants. The preferred antioxidants to employ in the formulation of the invention are gallic acid esters, nordihydroguaiaretic acid (NDGA), BHT or Vitamin E.

Gallic acid esters possess a varying chain length dependent upon the particular alcohol moiety. The inhibition of the lipoxygenase by the gallic acid esters appears to be brought about by a complexation of the non-heme iron of the active site of the enzyme by the catechol grouping of the gallates. Inhibition of the arachidonate 5-lipoxygenase pathway can be achieved with methyl gallate to n-tetradecyl gallate at concentrations of 6.0 to 1.2 microMoles per Liter. Prostaglandin H synthase inhibition can be inhibited by longer chain lengths of the alcohol moiety, i.e., n-octyl gallate to n-heptadecyl gallate at concentrations of 25 to 32 microMoles per liter.

So, in addition to their well-known antioxidant activity, the alkyl gallates are potent dual inhibitors of lipoxygenase and prostaglandin H synthase with selectivity for lipoxygenases at sufficiently low concentrations.

The preferred gallic acid ester to inhibit lipoxygenase is propyl gallate in concentration ranges of 0.1% to 5%. The most preferred concentration of propyl gallate to inhibit lipoxygenase is 2.0%.

The preferred gallic acid ester to inhibit Prostaglandin H synthase is either n-octyl gallate or n-dodecyl gallate. The preferred concentration of n-octyl gallate or n-dodecyl gallate is 0.1% to 3%.

Nordihydroguaiaretic acid (NDGA) is a major constituent of the resinous exudates of *Larrea divaricata*, the creosote bush of the southwestern USA and Mexico. NDGA is an excellent antioxidant for fats and oils.

Vitamin E can function as a 5-lipoxygenase inhibitor and antioxidant. The concentration of Vitamin E should be at least five microMoles per liter. The preferred concentration of Vitamin E in the novel formulation is 0.1% to 3.0%. The most preferred concentration of Vitamin E is 2.0% by volume.

Pantothenic acid is essential to normal epithelial function. The topical use of dexpanthenol, the stable alcoholic analog of pantothenic acid, is based on good skin penetration and high local concentrations of dexpanthenol when administered in an adequate vehicle. Adjuvant skin care with dexpanthenol considerably improves the symptoms of skin irritation, such as dryness of the skin, roughness, scaling, pruritis, erythema, erosion/fissures over a three to four week period at concentrations of 5%. The preferred concentration of dexpanthenol is five percent by volume.

EXAMPLE I

A face wash containing 2% ZPT is formulated in a non-comedogenic carrier comprising water, cetyl alcohol, propylene glycol, sodium laureth sulfate, and stearyl alcohol.

The face wash may be applied to any area of the skin susceptible to acne. The face wash may be left on the skin from about three minutes to about fifteen minutes and then the area should be rinsed with clean water.

After the 'rinse' the user will apply a lotion, emulsion or cream that comprises ingredients of the current invention to inhibit or reverse abnormal keratinization, reduce excess sebum excretion mediated by androgens, and to reduce or inhibit undesirable proliferation of *Propionibacterium*.

EXAMPLE II

Wash-Off Formulation

The composition of a preferred face or body wash which is utilizable as a first step in a treatment regimen for acne vulgaris is exemplified below.

| Ingredient | Amount |
| --- | --- |
| Salicylic Acid | 0.50 grams |
| Zinc pyrithione | 2.00 grams (4.17 cc of 48% suspension) |
| Pluronic F 68 | 10.0 grams |
| HPMC | 0.50-1.50 grams (see note) |
| Cetylpyridinium chloride | 0.10 grams |
| Sodium laureth sulfate | 2.00 grams |
| Fragrance | Q.S. |
| Purified water, preferably deionized | Q.S. to 100 cc |

Note:
A sufficient amount of thickener (HPMC) is incorporated to achieve a viscosity of ≥1000 centipoises.

To prepare wash-off formulation, cetylpyridinium chloride and sodium laureth sulfate are dissolved in approximately 70 mL of purified, preferably deionized, water. Slowly, the Pluronic F68 is incorporated while stirring at medium speed. Next, the HPMC is added with constant stirring until fully incorporated. Salicylic acid, which has been pulverized to fine particle size, is then added to the mixture. Fragrance, if desired, is slowly added. Zinc pyrithione is stirred in until fully incorporated and then the mixture is brought to final volume with purified water. Mixing is continued at a higher speed for two to four hours to obtain a smooth suspension.

EXAMPLE III

Wash-off Formulation

The composition of an alternate preferred face or body wash which is utilizable as a first step in a treatment regimen for acne vulgaris is exemplified below.

| Ingredient | Amount |
| --- | --- |
| Salicylic Acid | 0.50 grams |
| Zinc pyrithione 48 percent suspension | 2.00 percent by weight (4.17 cc per 100 cc) |
| Pluronic F68 | 10 cc |
| Klucel HFNF | 0.50 grams |
| Cetylpyridinium chloride | 0.10 grams |
| Sodium laureth sulfate | 2.00 grams |
| Fragrance | Q.S. |
| Purified water, preferably deionized, water | Q.S. to 100 cc |

EXAMPLE IV

Wash-off Formulation

The composition of an additional alternate preferred face or body wash which is utilizable as a first step in a treatment regimen for acne vulgaris is exemplified below.

| Ingredient | Amount |
| --- | --- |
| Salicylic acid | 0.5% |
| Zinc pyrithione | 2.0% |
| Sodium laureth sulfate | 3.0% |
| Butylene glycol | 3.0% |
| Hydroxyethylcellulose | 1.0% |
| Glycereth-26 | 0.83% |
| Sodium hydroxide | 0.2% |
| Cetylpyridinium chloride | 0.1% |
| Sodium polynaththalenesulfonate | 0.083% |
| Purified, preferably deionized, water | Q.S. to 100% |

EXAMPLE V

Wash-off Formulation

The composition of another alternate preferred face or body wash which is utilizable as a first step in a treatment regimen for acne vulgaris is exemplified below.

| Ingredient | Amount |
|---|---|
| Salicylic acid | 0.5% |
| Zinc pyrithione | 2.0% |
| Cetyl alcohol | 3.0% |
| Sodium laureth sulfate | 2.0% |
| Propylene glycol | 1.0% |
| Stearyl alcohol | 1.0% |
| Glycereth-26 | 0.83% |
| Butylene glycol | 0.33% |
| Sodium hydroxide | 0.2% |
| Acrylates/C-10-30 alkyl acrylate crosspolymer | 0.1% |
| Sodium polynapthalenesulfonate | 0.083% |
| Purified, preferably deionized, water | Q.S. to 100% |

EXAMPLE VI

Leave-On Formulation

The preferred composition of a leave-on formulation, which is utilizable alone or preferably as a second step in a treatment regimen for acne vulgaris, is exemplified. A minimal formulation would use at least one ingredient from each of the A through D categories.

A. Prevention of comedogenesis
 i) Linoleic acid
 ii) Salicylic acid
 iii) Retinaldehyde
B. Androgen-Induced Excessive Sebum Production
 i) Inhibition of 5 alpha-reductase
   a) Unsaturated aliphatic fatty acids
   b) Combination of zinc salt and pyridoxine HCl
   c) Azelaic acid
   d) Polyphenols
   e) Isoflavones
   f) Lignans
   g) Green tea catechins
 ii) Inhibition of androgen metabolism with glycyrrhetinic acid
 iii) Inhibition of sebaceous gland excretion with arachidonic acid
 iv) Androgen receptor blockade
   a) Ethyl laurate
   b) Ethyl linoleic acid
   c) Beta-sitosterol
   d) Progesterone and/or spironolactone.
C. Elimination of *Propionibacterium acnes*
 i) Topical antibiotics using tetracyclines, erythromycin or clindamycin
 ii) Topical linoleic acid
 iii) Topical Glycerol monolaurate
 iv) Topical zinc pyrithione
   D. Follicular Reactivity and Inflammation
 i) Gallic acid esters
 ii) Vitamin E
 iii) BHT
 iv) Nordihydroguaiaretic acid
 v) Dexpanthenol

EXAMPLE VII

Leave-On Formulation

An example of a preferred leave-on formulation is provided below:

| Ingredient | Amount | Indication |
|---|---|---|
| Isopropyl alcohol-USP | 60.00 cc | Solvent |
| Klucel HF | 1.00 gram | Thickener |
| Emersol 305 | 4.00 cc | Abnormal keratinization |
| | | 5 alpha-reductase inhibition |
| | | Antibacterial |
| Salicylic Acid | 0.50 gram | Keratolytic |
| Dexpanthenol | 5.00 gram | Anti-inflammatory |
| Ethyl laurate | 4.00 cc | Androgen receptor blockade |
| Zinc Pyrithione | 0.25 gram | Antibacterial |
| 18 Beta-glycyrrhetinic acid | 2.00 gram | Inhibition of 17 B - OHD |
| BHT | 0.50 gram | Antioxidant |
| Vitamin E | 10,000 units | Antioxidant |
| Pyridoxine HCL | 1.00 gram | 5 alpha-reductase inhibition |
| Zinc Sulfate | 1.00 gram | 5 alpha-reductase inhibition |
| Lauryl gallate | 100 mg/mL | 5 alpha-reductase inhibition |
| Octyl gallate | 100 mg/mL | 5 alpha-reductase inhibition |
| Beta-Sitosterol | 1.00 gram | Androgen receptor blockade |
| Glycerin | 3.00 grams | Humectant |
| Purified water, preferably deionized | Q.S. to 100 cc | |

To prepare the leave-on formulation: first, the salicylic acid, dexpanthenol, and ethyl laurate are dissolved in the isopropyl alcohol. Second, the Emersol 305, Vitamin E, BHT, lauryl gallate, octyl gallate and beta-sitosterol are mixed together, then pulverized 18-beta-glycyrrhetinic acid is added, and mixed well. With constant stirring, the Emersol mixture is added to the salicylic acid mixture. The zinc sulfate, pyridoxine HCl and glycerin are dissolved in approximately 20 mL of purified, preferably deionized, water, then with rapid stirring, the aqueous mixture is added to the alcohol mixture. While stirring at medium speed, Klucel HF powder is slowly sprinkled onto the mixture, and stirring is continued until the Klucel is fully incorporated, then the zinc pyrithione is slowly added and mixed well. Sufficient purified water is added to attain final volume, the container is covered and mixing is continued for four to six hours.

EXAMPLE VIII

Leave-On Formulation

An example of an alternate preferred leave-on formulation is provided below:

| Ingredient | Amount | Indication |
|---|---|---|
| Isopropyl alcohol-USP | 60.00 cc | Solvent |
| Klucel HFNF | One gram | Thickener |
| Emersol 305/315 | 2.00 cc | Comedolytic |
| | | 5 alpha-reductase inhibition |
| | | Antibacterial |
| Salicylic acid | 0.5 grams | Keratolytic |
| Ethyl laurate | 1.00 cc | Androgen receptor blockade |
| Zinc pyrithione 48% Suspension | 2.00% by weight 4.17 cc/100 cc | Antibacterial |
| Propyl gallate | 2.00 grams | Antioxidant |
| | | Anti-Inflammatory |
| Purified water, preferably deionized | Q.S. to 100 cc | |

Preparation of the formulation is as follows. Initially, the isopropyl alcohol, 10 cc of water and Klucel HFNF are stirred slowly until all the Klucel is completely hydrated. Next, the salicylic acid and propyl gallate are added until these components are solubilized. Afterward, the Emersol 305 or Emersol 315 is added and mixed well. The zinc pyrithione is added from a 48% micro-fine suspension with high shear. Lastly, purified water, preferably deionized, is added to bring the volume to 100 cc.

EXAMPLE IX

Leave-On Formulation

An example of an alternate preferred leave-on formulation is provided below.

| Ingredient | Concentration | Indication |
|---|---|---|
| Isopropyl alcohol-USP | 55.00 cc | Solvent |
| Salicylic Acid | 0.50 grams | Abnormal desquamation |
| Emersol 305/315 | 2.00 cc | Comedolytic |
| | | 5 alpha-reductase inhibition |
| | | Antibacterial |
| Zinc sulfate | 1.00 gram | 5 alpha-reductase inhibition |
| Pyridoxine HCL | 1.00 gram | 5 alpha-reductase inhibition |
| Dexpanthenol | 5.00 cc | Anti-inflammatory |
| Glycerol monolaurate | 2.00 grams | Antibacterial Emollient |
| Ethyl laurate | 1.00 cc | Androgen receptor blockade |
| Klucel HFNF | 1.00 gram | Thickener |
| Propyl gallate | 2.00 grams | Anti-Oxidant Anti-inflammatory |
| Zinc pyrithione, 48% Suspension | 2.00 percent by weight (4.17 cc/100 cc) | Antibacterial |
| Purified water, preferably deionized | Q.S. to 100 cc | |

The mode of mixing the ingredients is as follows. Isopropyl alcohol and 10 cc of water are stirred rapidly while slowly adding Klucel HFNF. Once the Klucel is hydrated, the alcohol soluble ingredients are mixed and stirred until dissolved. The water soluble zinc sulfate and pyridoxine HCl are solubilized in 10 cc of water and added to the mixture. Under high shear, the zinc pyrithione is added slowly. Lastly, the remainder of the deionized water is added to Q. S. to 100 cc.

EXAMPLE X

Leave-On Formulation

An example of another alternate preferred leave-on formulation is provided below.

| Ingredient | Amount | Indication |
|---|---|---|
| Isopropyl alcohol-USP | 50.00 cc | Solvent |
| Emersol 305/315 | 2.00 cc | Abnormal keratinization 5 alpha-reductase inhibition Antibacterial |
| Pyridoxine HCL | 1.00 gram | 5 alpha-reductase inhibition |
| Zinc sulfate | 1.00 gram | 5 alpha-reductase inhibition |
| Glycerol monolaurate | 2.00 grams | Antibacterial Emollient |
| 18 Beta glycyrrhetinic acid | 2.00 gram | Inhibition of 17 B-OHD |
| Retinaldehyde | 0.10 cc | Inhibit comedogenesis |
| Dexpanthenol | 5.00 cc | Anti-inflammatory |
| Ethyl laurate | 4.00 cc | Androgen receptor blockade |
| Beta-Sitosterol | 1.50 gram | Androgen receptor blockade |
| Klucel HFNF | 1.00 gram | Thickener |
| Propyl Gallate | 2.00 grams | Antioxidant Anti-inflammatory |
| Glycerin | 1.00 to 5.00 cc | Humectant |
| Silicone | 1.00 cc | Cosmetic feel |
| Lactic Acid (88%) | Q.S. to pH 4 | Enhanced antibacterial effect |
| Fragrance | Q.S. | Odor control of Emersol 305 |
| Salicylic Acid | 0.50 to 2.0 grams | Keratolytic |
| Zinc pyrithione; 48% Suspension | 0.25 percent | Antibacterial Anti-seborrhea |
| Purified water, preferably deionized | Q.S. to 100 cc | |

EXAMPLE XI

Leave-On Formulation

An example of another alternate preferred leave-on formulation is provided below.

| Ingredient | Amount |
|---|---|
| Salicylic acid | 0.5% |
| Zinc pyrithione, 48% Suspension | 0.25% |
| Isopropyl alcohol | 60.0% |
| Ethyl laurate | 5.0% |
| Linoleic acid | 5.0% |
| Glycyrrhetinic acid | 2.0% |
| Panthenol | 2.0% |
| Tocopherol acetate | 1.0% |
| Hydroxypropylcellulose | 1.0% |
| Zinc sulfate | 1.0% |
| Glycereth-26 | 0.5% |
| Pyridoxidine HCl | 0.5% |
| Butylene glycol | 0.2% |
| Acrylates/C-10-30 alkyl acrylate crosspolymer | 0.01% |
| Sodium polynapthalenesulfonate | 0.01% |
| Sodium hydroxide | 0.01% |
| Fragrance | 0.2% |
| Purified, preferably deionized, water | q.s. to 100% |

The formulations illustrated in the above Examples can be varied according to the conception of the invention as disclosed herein and serve only to illustrate representative formulations.

EXAMPLE XIII

Addition of other Ingredients

Although not necessary for the typical case of acne vulgaris, it may be desirable to include a topical antibiotic in one of the formulations of the invention. For example, in the case of patients with cystic acne, it may be desirable to include progesterone and/or spironolactone. If such products are incorporated into the invention, a prescription may be required for dispensing to the patient.

Though not preferred for the reasons stated above with respect to antibiotic resistance and the effectiveness of the non-antibiotic components included in the formulation against *P. acne*, in some cases a topical antibiotic may be desired in a formulation to address a particular case of skin disorder. A topical antibiotic such as a tetracycline, erythromycin or clindamycin could be added to the formulation which would likely change the method of distribution from over-the-counter to prescription only.

EXAMPLE XIV

Treatment of Acne Vulgaris

Treatments used in the following experiments were formulated as follows:

Treatment 1: A two-part regimen. Treatment Part 1 is a skin-wash using a solution of a non-comedogenic carrier comprising water, cetyl alcohol, propylene glycol, sodium laureth sulfate, and stearyl alcohol. Active ingredients salicylic acid (0.5%) and zinc pyrithione (2.0%) are added to the aforementioned suitable carrier. This formulation is left on the skin for 15 minutes followed by rinsing with clear water. Treatment Part 2 consists of a preparation of 0.5% salicylic acid and 0.25% zinc pyrithione as the primary active ingredients, with 7-beta-glycerrhetinic acid, propyl gallate, and Emersol 305 as additional ingredients. Treatment Part 2 is applied to the skin and left in contact with the treated area.

Treatment 2: A two-part regimen. Treatment Part 1 is a skin-wash composed of a non-comedogenic carrier comprising water, cetyl alcohol, propylene glycol, sodium laureth sulfate, and stearyl alcohol, with salicylic acid (0.5%) and zinc pyrithione (2.0%) as the active ingredients, which is left on the skin for 15 minutes followed by rinsing with clear water. Treatment Part 2 consists of a preparation of salicylic acid (0.5%), zinc pyrithione (0.25%), pyridoxine HCL, 18 beta glycyrrhetinic acid, glyceryl monolaurate, propyl gallate, dexpathenol, zinc sulfate, beta-sitosterol, ethyl laurate, silicone, HPMC, Emersol 305, glycerine, isopropyl alcohol, polawax, fragrance, and purified, preferably deionized, water. Treatment Part 2 is applied to the skin and left in contact with the treated area.

Treatment 3: A two-part regimen. Treatment Part 1 is a skin-wash composed of a non-comedogenic carrier comprising water, cetyl alcohol, propylene glycol, sodium laureth sulfate, and stearyl alcohol, with salicylic acid (0.5%) and zinc pyrithione (2.0%) as the active ingredients, which is left on the skin for 15 minutes followed by rinsing with clear water. Treatment Part 2 consists of a preparation of salicylic acid (0.5%) and zinc pyrithione (0.25%) as the primary active ingredients, with Klucel HFNF, Emersol 305, ethyl laurate, propyl gallate, isopropyl alcohol, deionized water and Shower Fresh Fragrance as additional ingredients. Treatment Part 2 is applied to the skin and left in contact with the treated area.

Patient Example A

Two fourteen year old girls presented to a physician with mild papulo-pustular acne which was documented by the physician. They reported their acne was refractory to treatment with a commercially available acne treatment which consists of: (1) an oil-free cleanser listing as its active ingredient benzoyl peroxide 2.5%, (2) an alcohol-free toner containing water (aqua), glycolic acid, *hamamelis virginiana* (witch hazel) extract, *anthemis nobilis* flower extract, *rosa canina* fruit extract, *aloe barbadensis* leaf juice, sodium PCA, panthenol, glycerin, propylene glycol, allantoin, polysorbate-20, hydroxyethylcellulose, sodium hydroxide, benzophenone-4, tetrasodium EDTA, methylparaben, propylparaben, imidazolidinyl urea, fragrance (parfum), blue 1, yellow 5, and (3) a repairing lotion containing the active ingredient: benzoyl peroxide 2.5%. They reported that the product had improved their acne but had not alleviated the problem.

The girls agreed to participate in a trial wherein they would continue to use the same commercial product they had been using only on one of the sides of their faces but to begin using only the formulations according to the present invention on the other sides of their faces. The girls were provided with a face wash made according to Example II and instructed to utilize daily as stated in the Example. After using the face wash as directed, the girls were instructed to apply a leave-on product according to Example VIII.

The patients returned to the clinic in two weeks for evaluation by the physician. Both were found to be completely clear of comedones, papules or pustules, and no difference was detected between the sides of their faces. Upon questioning, the physician discovered that the patients noticed a marked improvement on the sides of their faces where they had applied the experimental formulations of the invention and they had therefore ceased using the commercial product on the other sides of their faces. They began using only the experimental product on both sides of their faces as they wanted to rid their faces of the acne completely. They used the novel formulations on both sides of their faces with complete resolution of their acne.

Patient Example B

A 24 year old female who presented with severe pimples and mild acne of four years' duration was tested with the formulation of the invention. The current treatment being used was an over-the-counter solution as used by the patients in Patient Example A. Previous treatments used were tretinoin gel and isotretinoin capsules. Treatment took place over 226 days using Treatments 1, 2, and 3. All regimens were to be applied topically twice a day; at morning and before going to bed. Treatment 1 was the initial formulation used. The patient reported after two days that her skin had become significantly less inflamed. After two weeks, the patient reported significant clearing of the skin. Two months after the initial appointment, the patient returned for a follow-up appointment and the treated area was markedly improved. One month later, the patient was placed on Treatment 2. Patient reported no change in acne reduction over Treatment 1. In August, the patient was placed on Treatment 3. Three months later, the patient was re-evaluated and showed marked worsening as compared to Treatments 1 and 2; the patient's skin appeared as it had during the initial examination. Patient was placed back on Treatment 2. Three days later, patient reported that her skin condition was markedly improved; her face felt better and inflammation was significantly reduced.

Patient Example C

A 23 year old female with pimples of one year's duration, who had not seen a Board-Certified Dermatologist, was tested with the formulation of the invention. The current treatment being used was an over-the-counter solution. Previous treatment used was drospirenone and ethinyl estradiol tablets. Treatment took place over three weeks using Treatment 3. Regimen was to be applied topically twice a day; at morning and before going to bed, on one half of the face while the commercial product she had been using was to be applied to the other side of her face. Marked improvement of the patient's acne was noted during a follow-up visit. Upon questioning, the physician discovered that the patient noticed a marked improvement on the side of the face where she had applied the experimental formulation of the invention and had ceased using the commercial product on the other side of the face after four days. She began using only the experimental product on both sides of her face as she wanted to rid her face of the acne completely. She used the novel formulations on her entire face with major resolution of her acne. At the final checkup only a few small comedones remained.

Patient Example D

A 46 year old white male with pimples and skin inflammation in the moustache and beard areas of his face of thirty years' duration was tested with the formulation of the invention. Current treatment being used was an over-the-counter solution containing benzoyl peroxide. Previous treatment used was oral tetracycline tablets prescribed by a Board-Certified Dermatologist. The treatment took place over 48 days with a full-face trial of Treatment 3. Regimen was to be applied topically twice a day; at morning and before going to bed, on the entire face. Over the course of several appointments over the next 48 days, patient's acne and inflammation nearly disappeared entirely.

Patient Example E

A 14 year old female with simple acne of three years' duration presented and was tested with a formulation according to the invention. Current treatment being used was an over-the-counter solution containing benzoyl peroxide. Previous treatment used was a clindamycin solution prescribed by a Board-Certified Dermatologist, though the patient did not finish the course of the medication. Treatment took place over two weeks with a half-face trial of Treatment 3. For the duration of the treatment, patient applied her previous benzoyl peroxide regimen to the other half of her face. Regimen was to be applied topically twice a day, at morning and before going to bed. At the two-week re-evaluation, her face had markedly improved to the point of being mostly clear of blemishes.

I claim:

1. A kit for treatment of acne, consisting essentially of:
   a. a first container of about 1.0% to about 2.5% zinc pyrithione; and
   b. a second container of at least 0.25% zinc pyrithione, therapeutically effective amounts of linoleic acid, and a gallic acid ester selected from the group consisting of propyl gallate, n-octyl gallate, n-dodecyl gallate, and combinations thereof.

2. The kit according to claim 1, wherein the contents of said first container are in cream form.

3. The kit according to claim 1, wherein the contents of said second container are in cream form.

4. The kit according to claim 1, wherein the contents of said first container are in lotion form.

5. The kit according to claim 1, wherein the contents of said second container are in lotion form.

6. The kit according to claim 1, wherein the contents of said first container are in emulsion form.

7. The kit according to claim 1, wherein the contents of said second container are in emulsion form.

8. A kit for treatment of acne, consisting essentially of:
   a. a first container having salicylic acid and about 1.0% to about 2.5% zinc pyrithione; and
   b. a second container of at least 0.25% zinc pyrithione, therapeutically effective amounts of linoleic acid, and a gallic acid ester selected from the group consisting of propyl gallate, n-octyl gallate, n-dodecyl gallate, and combinations thereof.

9. The kit according to claim 8, wherein the contents of said first container are in cream form.

10. The kit according to claim 8, wherein the contents of said second container are in cream form.

11. The kit according to claim 8, wherein the contents of said first container are in lotion form.

12. The kit according to claim 8, wherein the contents of said second container are in lotion form.

13. The kit according to claim 8, wherein the contents of said first container are in emulsion form.

14. The kit according to claim 8, wherein the contents of said second container are in emulsion form.

15. A kit for treatment of acne, consisting essentially of:
   a. a first container of about 1.0% to about 2.5% zinc pyrithione; and
   b. a second container of at least 0.25% zinc pyrithione, therapeutically effective amounts of linoleic acid, and a gallic acid ester selected from the group consisting of propyl gallate, n-octyl gallate, n-dodecyl gallate, and combinations thereof, and
   therapeutically effective amounts of an additional active ingredient selected from the group consisting of: salicylic acid, retinaldehyde, gamma-linolenic acid, cis 4,7,10,13,16,19-docosahexaenoic acid, cis-6,9,12,15-octatetraenoic acid, arachidonic acid, alpha-linolenic acid, palmitoleic acid, oleic acid, myristoleic acid, zinc salt, pyridoxine hydrochloride, azelaic acid, green tea catechins, flavonoids, isoflavonoids, ethyl laurate, ethyl linoleate, beta-sitosterol, progesterone, spironolactone, Vitamin E, nordihydroguaiaretic acid, dexpanthenol, glycyrrhetinic acid, and combinations thereof.

16. The kit according to claim 15, wherein the contents of said first container are in cream form.

17. The kit according to claim 15, wherein the contents of said second container are in cream form.

18. The kit according to claim 15, wherein the contents of said first container are in lotion form.

19. The kit according to claim 15, wherein the contents of said second container are in lotion form.

20. The kit according to claim 15, wherein the contents of said first container are in emulsion form.

21. The kit according to claim 15, wherein the contents of said second container are in emulsion form.

* * * * *